(12) United States Patent
Rambod et al.

(10) Patent No.: US 8,200,313 B1
(45) Date of Patent: Jun. 12, 2012

(54) APPLICATION OF IMAGE-BASED DYNAMIC ULTRASOUND SPECTROGRAPHY IN ASSISTING THREE DIMENSIONAL INTRA-BODY NAVIGATION OF DIAGNOSTIC AND THERAPEUTIC DEVICES

(75) Inventors: Edmond Rambod, Los Angeles, CA (US); Daniel Weihs, Haifa (IL)

(73) Assignee: Bioquantetics, Inc., Los Angeles, CA (US)

( * ) Notice: Subject to any disclaimer, the term of this patent is extended or adjusted under 35 U.S.C. 154(b) by 827 days.

(21) Appl. No.: 12/286,570

(22) Filed: Oct. 1, 2008

(51) Int. Cl.
*A61B 5/05* (2006.01)
*A61B 8/00* (2006.01)

(52) U.S. Cl. .................. 600/424; 600/441; 600/443

(58) Field of Classification Search .......... 600/437–461, 600/420, 423, 424, 427, 431, 463, 466, 467; 601/2; 73/584, 589
See application file for complete search history.

(56) References Cited

U.S. PATENT DOCUMENTS

| | | | | |
|---|---|---|---|---|
| 5,425,370 | A * | 6/1995 | Vilkomerson | 600/463 |
| 5,715,822 | A * | 2/1998 | Watkins et al. | 600/422 |
| 5,868,673 | A * | 2/1999 | Vesely | 600/407 |
| 6,211,429 | B1 * | 4/2001 | Machaty et al. | 800/24 |
| 7,517,315 | B2 * | 4/2009 | Willis | 600/442 |
| 7,927,300 | B2 * | 4/2011 | Tanaka | 604/22 |
| 2004/0230111 | A1 * | 11/2004 | Smith et al. | 600/407 |

* cited by examiner

*Primary Examiner* — Brian Casler
*Assistant Examiner* — Shahdeep Mohammed
(74) *Attorney, Agent, or Firm* — Thomas I. Rozsa (57) ABSTRACT

Using Image-based Dynamic Ultrasound Spectrography (IDUS®) technology, the intrabody monitoring and positioning of an inserted catheter is achieved by coupling a thin micron-size polymeric wire to the catheter with 100-500 micron metallic cylinder attached to the tip of the wire. The area of interest is imaged and subsequently stimulated using specialized stimulation schemes delivered by an imaging ultrasound transducer. The targeted metallic tip is stimulated and emanates a unique acoustic response (signature) corresponding to its mechanical and material properties. Because of the fundamental structural differences between the targeted metallic tip and its surroundings, its unique resonant frequency signature can be analyzed and differentiated relative to the surrounding soft tissue, the wire and the catheter itself so that the location of the catheter in the body can be determined.

27 Claims, 2 Drawing Sheets

Figure 1: Schematic presentation of the present invention of IDUS for intrabody catheter positioning

STEP I - Two or three-dimensional ultrasound imaging of the general area where the catheter with the attached wire and metallic tip has been inserted into

STEP II – Stimulation of the targeted area where the metallic tip of the thin wire is located by specialized ultrasound amplitude-modulated schemes STEP III – The targeted and stimulated metallic tip produces unique acoustic signature corresponding to its natural resonant frequency STEP IV – The emitted acoustic signals are continuously monitored and recorded by sensitive and specialized detectors placed on the surface of the body near the area where the stimulation transducer is located, and spectral analyses performed STEP V – Real-time correlation between the recorded signals and pre-determined frequency database to identify and characterize the targeted metallic tip and its three-dimensional location.

Figure 2: IDUS® for intrabody catheter positioning – The sequence

APPLICATION OF IMAGE-BASED DYNAMIC ULTRASOUND SPECTROGRAPHY IN ASSISTING THREE DIMENSIONAL INTRA-BODY NAVIGATION OF DIAGNOSTIC AND THERAPEUTIC DEVICES

BACKGROUND OF THE INVENTION

1. Field of the Invention

The present invention relates to the field of detecting and localization of a catheter inserted into the human body for medical diagnosis, follow up and treatment.

2. Description of the Prior Art

In general, detection of the exact position of a catheter inserted in the blood vessels within the human body is important for different treatment and diagnosis purposes. Detection of a catheter in the human body has been performed using different imaging modalities in the prior art and there have been several techniques currently in active use. One of such techniques utilizes a thin, micron-size metallic tip attached to a micro-size polymeric wire and coupled to and inserted with a guided catheter into the blood vessels within the body. The inserted catheter into the blood vessel and the coupled wire with metallic tip are continuously monitored by ionizing X-ray or computer tomography (CT) modalities for localizing their three-dimensional position.

SUMMARY OF THE INVENTION

The present invention is based on the utilization of externally produced, noninvasive Image-Based dynamic ultrasound spectrography (IDUS™) for real-time imaging, targeting, stimulation and positioning of a micron-size metallic tip attached to a polymeric wire which is coupled with a catheter and inserted into blood vessels within the body. The purpose of this design is to: 1) target, 2) detect and 3) determine the three-dimensional positioning of the metallic tip within the blood vessel within the body for real-time diagnosis and guidance of various medical treatment and procedures.

It has been discovered, according to the present invention, that the improved technique to target and locate the metallic tip of the thin wire includes the utilization of disposable stickers that house certain specialized receiving detectors that collect the radiated acoustic signature/s from the stimulated metallic tip.

It has further been discovered, according to the present invention, that in the preferred embodiment, at least three reusable sensors (receivers) are firmly housed within the disposable stickers. Three sensors are required to determine the X-Y-Z coordinates of the exact location of the targeted metallic tip within the blood vessel within the body. Additional sensors may be used for correcting any errors in determining the X-Y-Z coordinates by the other three sensors. Another such sensor may be positioned within the imaging scanner and used to provide a reference vertical axis to: 1) determine the depth of the location where the targeted metallic tip is detected and 2) relative to which the said X-Y-Z coordinates are determined. In the present invention, this vertical axis is important to ensure that the positioning of the targeted metallic tip within the body is performed relative to the orientation and position of the body.

It has also been discovered, according to the present invention, that once the self-adhesive stickers and the housed sensors are positioned around the area of interest on the body, an ultrasound transducer (scanner) will then scan the areas of interest creating a B-mode image and looking for the targeted metallic tip. The stimulation mode can start subsequently to the imaging mode or simultaneously with the imaging mode and once a first-hand assessment of the emitted resonant frequency from the targeted metallic tip is detected, the scanner will remain steady on the body, the imaging mode of the said Image-Based Dynamic Ultrasound Spectrography (IDUS™) system is turned off and only the stimulation mode is activated. The area of interest will then be stimulated by a swept band of frequencies at a given range corresponding to the natural frequency of said metallic tip and modulated with a megahertz (1-14 MHz) carrier frequency to precision localization of the targeted metallic tip. The acoustic response from the targeted metallic tip will be monitored and recorded in real time and will appear as spectra where the peak frequency/ies will be recorded and spectrally analyzed. The recorded peak frequency/ies will then be compared in real-time with a predetermined database of frequencies obtained experimentally and corresponding to the specific metallic tip. A pre-programmed color-coded scheme will then be applied to color the site on the B-mode ultrasound image where the targeted metallic tip has been detected.

It has further been discovered that emitted frequencies from the targeted soft tissue is estimated at few Hertz (1-50 Hz), whereas the corresponding emitted frequencies from a targeted metallic tip is estimated to be in the range of 500 Hz to 20 KHz. It has also been discovered according to the present invention that the modulated frequency band used to stimulate the targeted metallic tip of a thin wire is not in the range that can stimulate the soft tissue or the polymeric wire and therefore, the site with metallic tip is distinguished by a unique set of frequencies from the surrounding tissue.

It has further been discovered, according to the present invention, that utilizing specialized localization methodology the exact three dimensional position of the targeted metallic tip of the polymeric wire is determined based on the signals received by the receiving sensors and analyzed respectively. The exact three-dimensional position of the metallic tip will be displayed on the B-mode image and marked for future reference and follow up.

It is an object of the present invention to provide a methodology for the detection and localization of the targeted metallic tip of a polymeric wire through a precise method of bi-modal medical ultrasound imaging, stimulation and spectrography which will enable the system to detect the targeted metallic tip of a thin polymeric wire coupled with a catheter, and the precise location of the targeted metallic tip.

It is a further object of the present invention to provide a method and system that provides bi-modal image guided stimulation of a targeted metallic tip within the blood vessels within the body to determine the location of the metallic tip within the body.

It is a further object of the present invention to provide real time qualitative imaging of the targeted area where the catheter and the attached metallic tip are assumed to be and quantitative data about the different structures (i.e., polymeric wire, catheter, and surrounding tissues) within the targeted area.

It is also an object of the present invention to provide a methodology to locate a targeted metallic tip attached to a thin wire and coupled to a catheter inserted into the blood vessels within the body without providing the drawbacks of other imaging and screening modalities. Contrary to other modalities, the present invention offers a noninvasive, having no ionization radiation, being safe, reliable, cost-effective, not Doppler based, not angular-dependent and being portable, suitable for field applications and suitable for operating room conditions.

It is a further object of the present invention to provide a pre-determined series of frequency map information which is programmed into the system so that once a targeted metallic tip is located and once its peak response frequency is determined, the peak response frequency can be compared to a preset series of mapped frequencies for correlative detection and site identification.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a schematic diagram of the present invention Image-Based Dynamic Ultrasound Spectrography (IDUS™) technology demonstrating the insonification procedure imposing by the modulated ultrasound frequency on a targeted metallic tip coupled with a catheter inserted into the blood vessels within the body and the detection and analysis methodology of the response frequencies emanating from the targeted metallic tip. The method uses a combined ultrasound imaging and stimulation transducer to: 1) image the general targeted area of interest where the coupled catheter-metallic tip is inserted, 2) stimulate the area of interest by the specific scheme corresponding to the resonant frequency of the targeted metallic tip. The response emitted from the targeted metallic tip will then be sensed by the multiplicity of the detectors placed on the body and near the area where the insonifying transducer is for triangulation, analysis and three-dimensional localization of the metallic tip within the body. This would indicate the three-dimensional location of the catheter which is coupled with the metallic tip;

DETAILED DESCRIPTION OF THE PREFERRED EMBODIMENTS

The present invention is based on the utilization of externally produced, noninvasive remote image-based dynamic ultrasound spectrography (IDUS®) for real-time acoustic stimulation of a targeted thin metallic tip which can be 100 to 500 microns in diameter and length attached to a thin polymeric wire of the same dimensions that is inserted through a guided catheter into a blood vessel within the human body. The purpose of this design is to determine the exact three-dimensional positioning of the metallic tip within the blood vessel within the body, which will indicate the exact three-dimensional location of the tip of the attached catheter for guidance of various medical diagnosis, treatment and procedures.

The present invention is depicted in the enclosed FIG. 1 which is a schematic representation of the present invention as described below.

The invention for the noninvasive remote ultrasound localization of a guided catheter coupled with a metallic tip by real-time tracking of the metallic tip of a thin polymeric wire in the blood vessel is based on the insonification of the metallic tip by two or more ultrasound radiation waves differing slightly in frequency, to result in a low frequency force, applied onto the metallic tip. This low frequency radiation force will stimulate the metallic tip and instigate its vibration at frequencies typical of its natural resonant frequency, material and shape. The vibrational response of the targeted metallic tip which is related to the difference of the two or more transmitted frequencies (low frequency modulation), is measured by one or more noninvasive remote low frequency (kHz) specialized acoustic detector/s positioned on the body. This measurement allows the evaluation of the acoustic signatures, thus providing real-time information on the 3-dimensional positioning of the targeted metallic tip within the periodically moving or static blood vessel within the body. This technique involves two main components:

(i) The aiming high frequency (MHz) ultrasound insonifier/s, and (ii) The wide band, low frequency acoustic detectors Ultrasound radiation modalities with megahertz frequencies (MHz) have a very small wavelength, to demonstrate the necessary spatial resolution for exact targeting of the interrogated metallic tip of the polymeric wire. Generally, it is well known in the art that many metallic structures, especially those characterized by distinguished vibratory shapes, size and materials, manifest acoustic natural resonances at particular frequencies, which can serve as their unique acoustic signatures. The unique acoustic signature is strongly dependent on the size, structure, material strain coefficients and the submerging environment of the wire. These resonances can be experimentally measured by the stimulation of the modes of vibrations and listening to the radiated acoustic waves by known listening instrumentations, like our ears, microphones, accelerometers, etc. Additionally, such acoustic resonances can be theoretically predicted using different computer programs, like the Finite Elements Methods.

The present invention remotely measures the characteristic acoustic signature/s of the targeted and stimulated metallic tip attached to a thin wire with markedly different resonance characteristics, using megahertz ultrasound frequency (MHz) radiation, which is well known to be able to penetrate the human body and focus on the interrogated metallic tip with high resolution and precision. The active stimulation is done by amplitude modulation of the MHz carrier frequency with a KHz frequency corresponding to the resonant frequency of the metallic tip. Real-time continuous monitoring, detection and analysis of the emitted acoustic signature from the moving metallic tip of a thin wire within the blood vessel which can provide a single dimension position of the metallic tip, which in conjunction with other two-, dimensional imaging modalities (such as X-ray) provides a real-time three-dimensional positioning of the metallic tip as an indication for the spatial position of the guided catheter within the blood vessel within the body. According to the present invention, an alternate possibility is to use Time-of-Flight techniques, with multiple receivers (at least three) positioned on the body such as each individual receiving detector will provide a single dimension of the spatial position of the metallic tip within the body and wherein triangulation of multiple signals from multiple detectors will result in the three-dimensional positioning of the metallic tip by pure, non-invasive, non-ionizing, safe and precise ultrasound detection. Such a real-time, continuous and exact positioning of the metallic tip will indicate the spatial location of the attached catheter at any given time for a variety of diagnostic and therapeutic purposes. The advantage of this invention is in its spatial resolution and combination of ultrasound imaging and spectrography capabilities, which is safe compared to other ionizing X-ray-based imaging modalities.

The Rationale

The Image-Based Dynamic Ultrasound Spectrography (IDUS™) technology has already been shown to provide a real-time, safe, reliable and cost-effective diagnostic technique for detection of structural flaws in implanted medical devices. The fundamental concept of IDUS® the present invention is to excite the target externally and then measure its response by using specialized sensor/s. By measuring the emanating response of the target, its structural state can be determined relative to the surrounding environment.

The Principle

Figure 1:
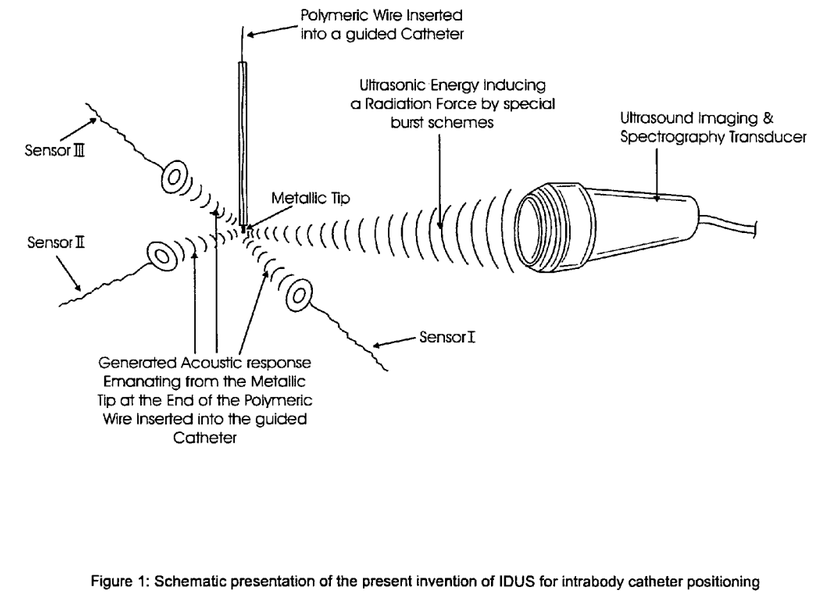

Image-Based Dynamic Ultrasound Spectrography (IDUS™) system is an active acoustic technology in which the targeted site is imaged first and then stimulated using proprietary and specialized ultrasound schemes delivered by the same ultrasound imaging transducer (see FIG. 1). The frequency response of the resulting stimuli is detected by a detector or a series of detectors positioned externally on the body and in the immediate vicinity of the transmitting transducer, and analyzed in real-time using proprietary algorithm.

The Sequence

Figure 2:
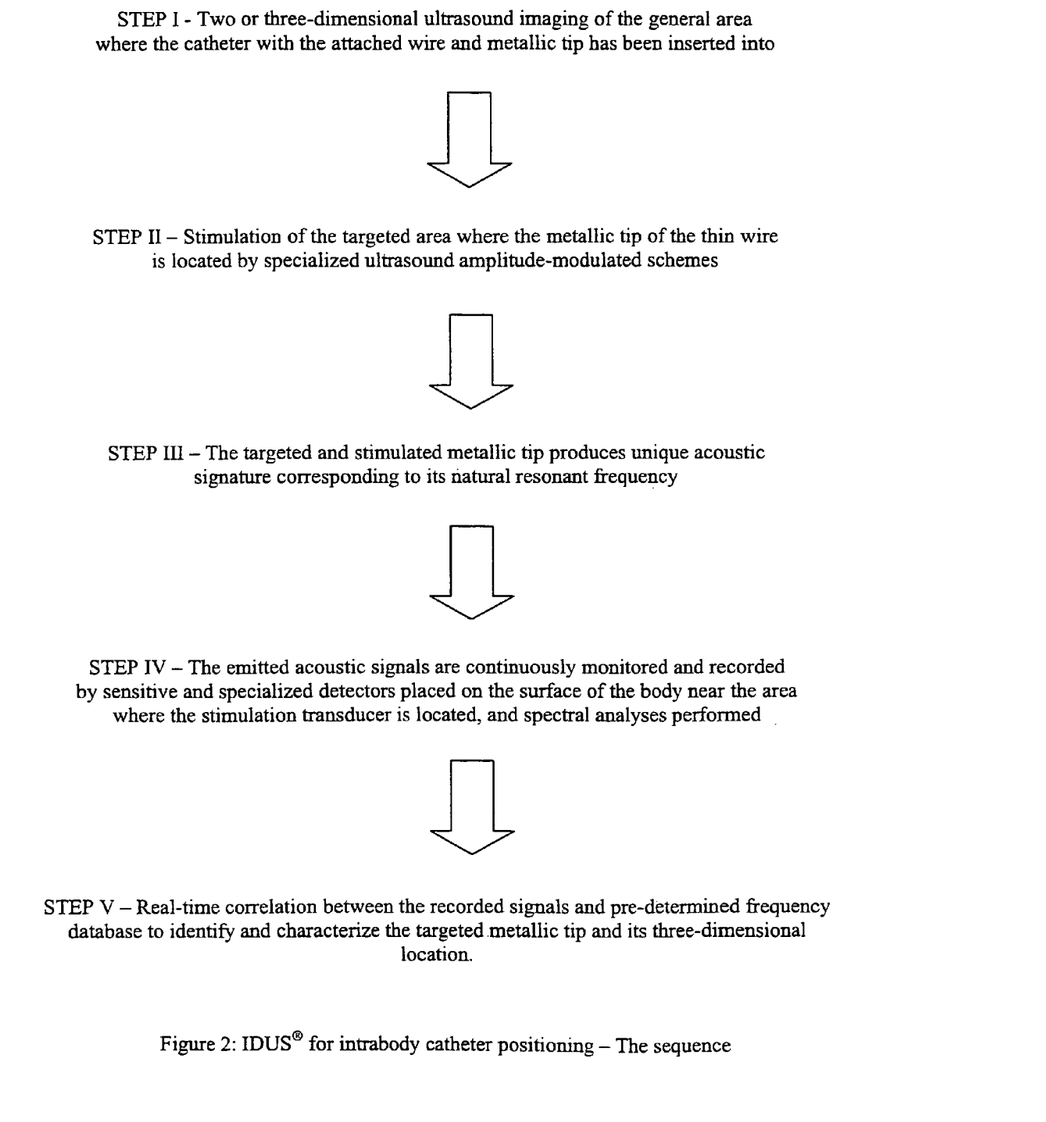
FIG. 2 is a flow diagram showing the sequence of the steps of the present invention.

Following the conventional ultrasound imaging, the Active Acoustics Approach (AAA) uses multiple ultrasound beams at differential frequencies to stimulate the target (FIG. 2, Steps I and II). By projecting these beams onto the object, an oscillating radiation point-force is applied onto the object, which in return produces unique acoustic signals (Step III). The emitted acoustic signal is recorded by a sensitive detector or a series of detectors located in the vicinity of the targeted object (Step IV). The recorded response is subsequently analyzed and compared with pre-defined frequency maps and characterized (Step V).

The present invention Image-Based Dynamic Ultrasound Spectrography (IDUS™) system is a platform technology that utilizes AAA to offer a real-time, bi-modal methodology based on non-invasively imaging of the area of interest (AOI), and A) Stimulating the AOI with specialized ultrasound-based waveform schemes, B) Performing spectral analysis of the target's response to external stimulation, C) Correlating the response with pre-existing frequency maps and identifying the target, and D) Navigating and positioning of the AOI in 3-dimension.

Identification of the target is performed according to its characteristic peak response frequency signature, which is unique to its mechanical and material properties (viscosity, elasticity, plasticity, visco-elasticity, etc). Based on the recorded acoustic fingerprint, the target is classified in different categories of frequency bands. In the present invention Image-Based Dynamic Ultrasound Spectrography (IDUS™), system, each of the defined categories is investigated by sweeping the ultrasound energy imposed onto the target in each frequency band. The response frequency could deviate from a few Hz to several KHz and the response could be in the form of a narrow peak or a band of frequencies, based on the mass density of the targeted area/material. The present invention Image-Based Dynamic Ultrasound Spectrography (IDUS™) system possesses the potential of becoming a complete and unique methodology for real-time, three-dimensional localization of a catheter inserted in the human body for diagnosis and treatment.

The Image-Based Dynamic Ultrasound Spectrography (IDUS™) System for Real-Time Intrabody Catheter Positioning The present invention Image-Based Dynamic Ultrasound Spectrography (IDUS™) system has been designed to stand alone as a dual-mode diagnostic ultrasound platform or be integrated to and perform in conjunction with a standard ultrasound imaging platform. The present invention Image-Based Dynamic Ultrasound Spectrography (IDUS™) system uses proprietary ultrasound technology to stimulate the area of interest (AOI) in the body where the catheter with the coupled wire and the metallic tip are inserted in the body and subsequently analyzes and characterizes the response frequency of the targeted metallic tip based on spectrography techniques. The dual-mode platform technology may utilize state-of-the-art ultrasound platforms and acoustic technologies for imaging, stimulating frequency sweeping, frequency recording and localizing the targeted metallic tip. Real-time spectral analysis determines the differentiated particular spectral resonance signature of the targeted metallic tip.

Using the present invention Image-Based Dynamic Ultrasound Spectrography (IDUS™) system, detection of a micron-size metallic tip of a thin wire coupled with a catheter will be done during a routine clinical ultrasound examination providing valuable quantitative information. Since the examination is cost-effective and does not expose the examinee to any ionizing radiation whatsoever, it can be repeated as many time as needed for guidance, more effective follow-ups and treatment. The main software components of the present invention Image-Based Dynamic Ultrasound Spectrography (IDUS™) system for three-dimensional intrabody catheter positioning are:

1) the software for frequency-sweeping stimulation scheme, and 2) the software for response frequency acquisition, data analysis, processing and 3-D navigation.

The most important hardware components of the present invention Image-Based Dynamic Ultrasound Spectrography (IDUS™) system are:

1) the specialized power amplifier, 2) the specialized surface frequency sensors (detectors), and 3) the modified imaging transducer.

The power amplifier is an integral part of any standard ultrasound platform which maybe modified to meet the present invention Image-Based Dynamic Ultrasound Spectrography (IDUS™) system specifications. The sensors have to be custom-made to meet the sensitivity requirements for the range of emitted resonant frequencies from the metallic tip attached to a thin wire. The only modification to the imaging transducer is related to the 3-D localization capability of the present invention Image-Based Dynamic Ultrasound Spectrography (IDUS™) system. Other devices required for implementation of the present invention Image-Based Dynamic Ultrasound Spectrography (IDUS™) system are standard components of any ultrasound platform and can be accommodated within the platform itself. These include: A) electronic filters, B) high-speed processors, C) display monitors and C) high-speed video card/s, a keyboard and a trackball.

It is important to note, that the present invention Image-Based Dynamic Ultrasound Spectrography (IDUS™) system also includes disposable, self-adhesive stickers, each attached to the body and house a sensors. The disposable stickers are made out of biocompatible material. The coupling of the stickers and the sensors to the body facilitate the sensors to firmly couple with the skin via a thin film. The film will prevent formation of an air gap between the sensor and the skin, thus enhancing returned data acquisition and eliminating the possibility of signal attenuation or distortion. It is expected that multiple (at least three) sensor used for catheter positioning in one examinee.

How Does It Work?

Imaging Mode—The imaging feature of an ultrasound platform provides a 2 or 3-dimensional B-mode (grayscale) image of the targeted area (commonly performed during any routine procedure). The image is obtained by using a linear-array transducer with a center frequency ranging from 1.0 megahertz (MHz) to 14 MHz depending on the application and depth of the AOI. Higher frequency provides imaging of smaller depth. For example, a 3 MHz transducer can provide images at depth of 12 to 15 centimeters in the body, whereas a 14 MHz transducer (typically used in pediatric applications) can provide images of targets at approximately 1.5 centimeters depth. The grayscale imaging resolution of the advanced ultrasound platforms are reasonably high and thus their improved mapping capabilities.

Stimulation Mode—Once the grayscale ultrasound image of the AOI (where the catheter is assumed to be) has been obtained and marked, the procedure is switched to the stimulation mode where the AOI (and the targeted metallic tip) is projected with specific ultrasound waveform (energy) scheme/s delivered by the present invention Image-Based Dynamic Ultrasound Spectrography (IDUS™) system via the same imaging transducer. By projection of the ultrasound energy scheme/s onto the target, an oscillating force is generated that sets the object to vibrate at or near its lowest natural frequency. The resulting vibration produces sound signals (a unique signature), which is received by a series of receiving sensors (at least three) positioned on the body in the vicinity of the ultrasound imaging scanner. A typical receiver is less than 25 millimeters in diameter. The emitted frequencies may vary from a few Hz to several KHz depending on the targeted metallic tip of the wire.

The present invention Image-Based Dynamic Ultrasound Spectrography (IDUS™) system analyzes the recorded signals from all sensors in real-time to identify maximum emitted frequencies. The maximum peak of the frequency spectrum is then compared to a pre-defined map of frequency/ies corresponding to targeted metallic tip. The pre-defined frequency map can be programmed into the ultrasound platform software. When a correlation between the recorded peak frequency and the programmed frequency map is found, the AOI on the B-mode image is color-marked according to a programmed color-coding scheme. By moving the ultrasound imaging transducer over the body around were the catheter is detected (according to the detected response frequency), the movement of the catheter can be traced and imaged in real-time.

A specific frequency map will be developed for each medical application of the present invention Image-Based Dynamic Ultrasound Spectrography (IDUS™) platform technology (breast, cardiac, vascular, orthopedic, etc.) and embedded into the ultrasound imaging platform database. The transition between different applications of the present invention Image-Based Dynamic Ultrasound Spectrography (IDUS™) is expected to be straightforward and will essentially be the same as done at present.

Unique Advantages of the Image-Based Dynamic Ultrasound Spectrography (IDUS™) System Non-invasive detection of differentiated materials in the targeted area can be achieved based on spectral analysis of the response frequencies as a result of external stimulation—The characteristics of the vibrations of various targets and resultant sound signals are different and distinguishable in different material and mediums. Thus, detection and classification of unique frequency signatures allows differentiation and diagnosis of mechanical characteristics.

Real-time imaging—Saves on time-consuming image acquisition and post-processing, and especially streamlines guided catheterization.

High sensitivity and specificity—Different targets have different and yet specific frequency response signatures corresponding to their state. These will result in enhanced sensitivity and specificity of the present invention Image-Based Dynamic Ultrasound Spectrography (IDUS™) technology.

User intuitive—The system is based on common ultrasound screening technology. Therefore, no complex or extraordinary training is required.

No ionizing radiation—IDUS®—Image-Based dynamic ultrasound spectrography allows prolonged procedures with no hazard of radiation involved in X-ray based screening modalities.

Low cost capital equipment—The system is based on conventional ultrasound imaging technology, and will be marketed by ultrasound manufacturers as a standalone system or as an integral part of a high-end ultrasound platform at acceptable premium price.

High accessibility for patient follow-up—The present invention Image-Based Dynamic Ultrasound Spectrography (IDUS™) system will be potentially available in every hospital, field and clinical setup currently hosting ultrasound equipment. Additionally, it may be used in operating rooms, cath labs, field hospitals and rural areas without a need for major real-estate and special infrastructure.

Cost-effective treatments—The reimbursement cost of the new modality is expected to be much lower than competing functional imaging modalities such as MRI.

3-D positioning—A unique advantage of the present invention Image-Based Dynamic Ultrasound Spectrography (IDUS™) system which will allow for better imaging when combined with 3-dimensional ultrasound capabilities or for better positioning and localization of the AOI by using GPS compatible technologies.

Defined in detail, the present invention is a non-invasive method, comprising: (a) a bi-modal ultrasound-based methodology of identifying and positioning in three-dimensional space, a micron-size metallic tip attached to a thin polymeric wire that is inserted through a guided catheter into a blood vessel within the body; (b) positioning one or more disposable biocompatible self-adhesive sticker or stickers on the body, each one containing a housing for retaining an acoustic receiving sensor which is positioned within the sticker; (c) the lower surface of each sensor housing is open and retains a thin transparent biocompatible plastic film which separates the receiving sensor from contacting skin on the body; (d) the lower surface of the sticker around the location of the receiving sensors is covered with biocompatible self-adhesive material coupled with a removable protective material selected from the group consisting of paper or plastic material; (e) the biocompatible self-adhesive material is exposed by peeling-off and removing the protective paper or plastic material; (f) positioning the disposable sticker on and around the area of interest on the human body and removably adhering the sticker onto the body so that the sensor housings and the thin film are firmly coupled with the skin of the body; (g) utilizing a bi-modal IDUS® functional imaging system with "Imaging Mode" and "Stimulation Mode"; (h) the IDUS® system is switched to its "Imaging Mode"; (i) a modified ultrasound imaging scanner is utilized to scan different segments of the area of interest and impact the body with ultrasound imaging frequencies in the range of 3 megahertz (MHz) to 14 MHz to image the segments of the body at each given time; (j) an ultrasound B-mode gray scale image is created whereby ultrasound frequencies are transmitted towards specific segments of the body and subsequently reflected from the specific segment of the body towards the scanner; (k) the scanner is then held stationary and the IDUS☐ system is switched to its "Stimulation Mode"; (l) the selected segment of the body is stimulated by a non-invasive burst or a chirp scheme delivered by the same imaging scanner; (m)

when the stimulation frequency is delivered as chirp scheme, one signal generator provides chirps of different frequency ranges while the other signal generator provides a fixed frequency so that due to the difference in the applied frequencies, certain acoustic forces are generated proportional to the natural frequency of targeted metallic tip that stimulates and vibrates the targeted metallic tip; (n) a single chirp is broken down into different segments so that the frequency scan occurs in a particular and controlled sequence called "one presentation" so that the chirps can scan the desired frequency spans and search for any resonance of the target in order to maximize the time for which each frequency span is introduced, which in turn increases the signal-to-noise ratio (S/N); (o) when the stimulation frequency is delivered as burst sweep form the data is acquired over time wherein a fixed megahertz frequency is applied to the targeted metallic tip of a polymeric wire in the form of a burst and another different megahertz frequency is incremented; (p) in detection of stationary wire and its metallic tip, said burst-sweep stimulation scheme is preferred wherein a first-hand estimate of the response is obtained and then a chirp frequency scheme is applied; (q) in either chirp or burst sweep schemes, the stimulation signal is swept over a pre-determined band of Hertz or kilohertz range frequencies and the frequencies are modulated on a megahertz ultrasound carrier frequency; (r) as a result of stimulation, the metallic tip of the wire produces acoustic signals specific to its resonant frequency and that are received by the receiving sensor or sensors attached to the stickers and positioned on the body; (s) utilizing an acoustic readout means whereby certain frequencies received by one or more of the sensors positioned on the disposable stickers; (t) the obtained emitted resonant frequency by each receiving sensor is compared in real-time with the pre-determined frequency for the metallic-tip; and (u) if a detected (received) frequency by sensor/s correlates with a predetermined frequency of the metallic tip of the wire, the targeted site on the B-mode image is color-coded using a predetermined color scheme and the exact coordinates of the site within the body is determined based on a snap-shot or continuous readout from every sensor using certain triangulation techniques to provide a point-in-time or continuous detection of the moving-metallic tip.

Defined broadly; the present invention is a non-invasive method, comprising: (a) a bi-modal ultrasound-based methodology of identifying and positioning in three-dimensional space, a micron-size metallic tip attached to a thin polymeric wire that is inserted through a guided catheter into a blood vessel within the body; (b) placing one or more disposable stickers around the area of the interest on the body; (c) positioning a receiving sensor within each sticker which is placed around and removably adhered to the skin, each sensor respectively coupled with a thin and transparent film which is firmly coupled to skin on the body by a layer of bio-compatible adhesive surrounding the thin film on the sticker; (d) utilizing a B-mode ultrasound scanner to scan the area of interest on the body creating a gray-scale B-mode image of the area of interest where the polymeric wire is located within the blood vessel within the body; (e) the transmitted ultrasound frequency being varied from 3 MHz to 14 MHz covering a range of depths; (f) once an image of the area of interest in obtained, the area of interest is marked and the imaging scanner is turned into a simultaneously B-mode imager and stimulating scanner; (g) the area of interest is then stimulated by a swept band of ultrasound frequencies generated by proprietary sequence of specialized schemes delivered by the same ultrasound imaging scanner; (h) the metallic tip of the wire traveling in the blood vessel within the body is stimulated by sequential frequency schemes resulting in emanating a characteristic response frequency proportional to its material and size; (i) monitoring the response in real time so that a spectrum including a peak resonant frequency is recorded and spectrally analyzed; (j) having the detected peak resonant frequency correlated with a predetermined database of predefined peak resonant frequencies to determine presence of the metallic tip of the wire, which may be invisible on the B-mode image; (k) if the detected response frequency or band of frequencies correlate with peak value or values in a predefined frequency signature map, the exact three-dimensional coordinates of the area from where the frequency or frequencies have been detected is marked on the B-mode image and colored according to particular predetermined color-coded scheme; and (l) utilizing certain specialized triangulation technique, the exact three dimensional position of the area of interest is determined at every point of time based on the signals received by the receiving sensors and analyzers respectively, with the exact three dimensional position of the targeted area continuously displayed on a B-mode image and recorded for future reference.

Defined more broadly, the present invention is a non-invasive method, comprising: (a) a bi-modal ultrasound-based methodology of identifying and positioning in three-dimensional space, a micron-size metallic tip attached to a thin polymeric wire that is inserted through a guided catheter into a blood vessel within the body; (b) positioning a multiplicity of acoustic receiving sensors on a sensor retaining means so that the acoustic receiving sensors are spaced apart from each other; (c) positioning the sensor retaining means on and around the area of interest so that the multiplicity of acoustic sensors are positioned on the human body; (d) utilizing a bi-modal IDUS□ functional imaging system which has an Imaging Mode and a Stimulation Mode; (e) utilizing the Imaging Mode of the IDUS□ with a modified ultrasound imaging scanner to scan different segments of the area of the interest and impact the area of interest with ultrasound imaging frequencies in the range of 1 megahertz to 14 megahertz to image segments of the human body at given times to thereby create an ultrasound B-mode gray scale image wherein ultrasound frequencies are transmitted toward specific segments of the human body and subsequently reflected from each specific segment of the human body toward the scanner; (f) utilizing the Stimulation Mode of the IDUS□ with said modified ultrasound imaging scanner and stimulating selected segments of the human body with a non-invasive chirp scheme delivered by the modified ultrasound imaging scanner utilizing two signal generators so that one signal generator provides chirps of different frequency ranges while the other signal generator provides a fixed frequency so that due to the difference in the applied frequencies, certain acoustic forces are generated proportional to the natural frequency of targeted metallic tip of a polymeric wire that stimulates and vibrates the targeted metallic tip; (g) a single chirp is broken down into different segments so that the frequency scan occurs in a particular and controlled sequence called "one presentation" so that the chirps can scan the desired frequency spans and search for any resonance of the target in order to maximize the time for which each frequency span is introduced to thereby increase the signal-to-noise ratio; (h) the stimulation signal is swept over a band of Hertz or kilohertz range frequencies and the frequencies are modulated on a megahertz ultrasound carrier frequency so that the metallic tip of a polymeric wire produces acoustic signals specific to their mass density and that are received by the acoustic receiving sensors and read out by an acoustic readout means to obtain response frequencies; and (i) real-time comparing and correlating the obtained response frequencies with a predetermined map of peak frequencies corresponding to the same metallic tip of a polymeric wire so that when a detected frequency correlates with a predetermined frequency in the frequency signature map, the targeted site of the metallic tip on the B-mode image is color-coded utilizing a predetermined color scheme and the exact coordinates of the site within the human body is determined.

Defined even more broadly, the present invention is a non-invasive method, comprising: (a) a bi-modal ultrasound-based methodology of identifying and positioning in three-dimensional space, a micron-size metallic tip attached to a thin polymeric wire that is inserted through a guided catheter into a blood vessel within the body; (b) positioning a multiplicity of acoustic receiving sensors, each retained on a sensor retaining means so that the acoustic receiving sensors are spaced apart from each other; (c) positioning the sensor retaining means on and around the area of interest on the human body; (d) utilizing a bi-modal IDUS□ functional imaging system which has an Imaging Mode and a Stimulation Mode; (e) utilizing the Imaging Mode of the IDUS□ with a modified ultrasound imaging scanner to scan different segments of the area of interest on the human body and impact the human body with ultrasound imaging frequencies in the range of 1 megahertz to 14 megahertz to image segments of the human body at given times to thereby create an ultrasound B-mode gray scale image wherein ultrasound frequencies are transmitted toward specific segments of the human body and subsequently reflected from each specific segment of the human body toward the scanner; (f) utilizing the Stimulation Mode of the IDUS□ with said modified ultrasound imaging scanner and stimulating selected segments of the human body with a non-invasive burst sweep form so that data is acquired over time wherein a fixed megahertz frequency is applied to the targeted polymeric wire with a micron-size metallic tip in the form of a burst and another different megahertz frequency is incremented to obtain a first hand estimate of the response; (g) the stimulation signal is swept over a band of Hertz or kilohertz range frequencies and the frequencies are modulated on a megahertz ultrasound carrier frequency so that targeted metallic tip produces acoustic signal or signals specific to its material and size and that the acoustic signal or signals are received by the acoustic receiving sensors and read out by an acoustic readout means to obtain and display response frequencies; and (h) real-time and continuous comparing and correlating the obtained response frequency or frequencies with a predetermined map of peak frequencies corresponding to similar metallic tip so that when a detected frequency correlates with a predetermined frequency in the frequency signature map, the targeted site on the B-mode image is color-coded utilizing a predetermined color scheme and the exact coordinates of the site within the human body is determined.

Defined even more broadly, the present invention is a non-invasive method, comprising: (a) a bi-modal ultrasound-based methodology of identifying and positioning in three-dimensional space, a micron-size metallic tip attached to a thin polymeric wire that is inserted through a guided catheter into a blood vessel within the body; (b) positioning a multiplicity of acoustic receiving sensors each on a sensor retaining means so that the acoustic receiving sensors are spaced apart from each other; (c) positioning the sensor retaining means on and around the area of interest on the human body; (d) utilizing a B-mode ultrasound scanner to scan the area of interest creating a gray-scale B-mode image of the area of interest with potential location of the thin polymeric wire; (e) the transmitted ultrasound frequency being varied from 3 MHz to 14 MHz covering a range of depths; (f) once an image of the area of interest in obtained, the scanner is maintained stationary relative to the body surface, the area of interest is marked and interrogated; (g) the area of interest is then stimulated by a swept band of ultrasound frequencies generated by proprietary sequence of specialized schemes delivered by the same ultrasound imaging scanner; (h) the metallic tip of the thin polymeric wire is then stimulated by sequential frequency schemes resulting in emanating a characteristic response frequency proportional to its material and size; (i) real-time and continuous monitoring of the response so that a spectrum including a peak resonant frequency is recorded and spectrally analyzed; and j) having the detected peak response frequency correlated with a predetermined database of predefined peak resonant frequencies to determine presence of the metallic tip of the micron-size polymeric wire in the blood vessel within the human body.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A non-invasive bi-modal ultrasound-based methodology of identifying and positioning in three-dimensional space comprising:
   a. attaching a micron-size metallic tip which functions as a target to a thin polymeric wire that is inserted through a guided catheter into a blood vessel within a body;
   b. positioning at least one disposable biocompatible and self-adhesive sticker on the body, each one containing a housing for retaining at least one acoustic receiving sensor;
   c. each acoustic receiving sensor housed within the at least one disposable sticker is separated from directly contacting the skin on the body by a thin, acoustically transparent biocompatible plastic film;
   d. one side of the at least one disposable sticker around a location of the at least one receiving sensor is coated with biocompatible adhesive material coupled with a removable protective material selected from the group consisting of paper and plastic material;
   e. the biocompatible adhesive material is exposed by peeling-off and removing the protective paper or plastic material;
   f. positioning the at least one disposable sticker on and around an area of interest on the body and removably adhering the at least one disposable sticker on the skin so that an acoustic sensor is housed within the disposable sticker and separated from the skin by a thin film which is firmly coupled with the skin of the body;
   g. utilizing a bi-modal image-based dynamic ultrasound spectrography system with an "Imaging Mode" and a "Stimulation Mode";
   h. the image-based dynamic ultrasound spectrography system is switched to its "Imaging Mode";
   i. a modified ultrasound imaging scanner is utilized to scan different segments of the area of interest in the body and impact the area of interest in the body with ultrasound imaging frequencies in the range of 1 megahertz (MHz) to 14 MHz to image the different segments of the area of interest in the body at each given time;

j. an ultrasound B-mode gray scale image is created whereby ultrasound frequencies are transmitted towards different segments of the area of interest in the body and subsequently reflected from the different segments of the area of interest in the body towards the modified ultrasound imaging scanner;

k. the modified ultrasound imaging acoustic scanner is then held stationary and the image-based dynamic ultrasound spectrography system is switched to its "Stimulation Mode";

l. the different segments of the area of interest in the body are stimulated by a non-invasive burst or a chirp scheme each delivered by the modified ultrasound imaging scanner to create a stimulation-induced frequency response;

m. when the stimulation frequency is delivered in the form of a chirp scheme, two signal generators are used, a first signal generator provides chirps of different frequency ranges while a second signal generator provides a fixed frequency so that due to a difference in the frequencies applied from the first and second chirp generators, certain acoustic radiation force is generated proportional to a natural frequency of targeted metallic tip that stimulates and resonates the targeted metallic tip;

n. a single chirp is broken down into different segments so that the frequency scan of different segments of the chirp stimulation occurs in a particular and controlled sequence called "one presentation" so that the chirps can scan a desired frequency span and search for any resonance of the micro-size metallic tip target in order to maximize a time for which each frequency span is introduced, which in turn enhances a signal-to-noise ratio (S/N);

o. when the stimulation frequency is delivered in the form of a burst sweep, data is acquired over time wherein a fixed megahertz frequency is applied to the targeted metallic tip of a polymeric wire as a burst and another different megahertz frequency is incremented;

p. in detection of stationary wire and its metallic tip, said burst-sweep stimulation scheme is preferred wherein a first-hand estimate of a response is obtained and then a chirp frequency scheme is applied;

q. in either chirp or burst sweep schemes, the stimulation signal is swept over a pre-determined band of Hertz or kilohertz range frequencies and modulated on a megahertz ultrasound carrier frequency;

r. as a result of stimulation, the metallic tip of the wire produces acoustic signals specific to its resonant frequency and the acoustic signals are received by the receiving sensor or sensors attached to the stickers and positioned on the body;

s. utilizing an acoustic readout means whereby certain frequencies received by one or more of the acoustic sensors positioned on the disposable stickers;

t. the emitted resonant frequency received by each acoustic receiving sensor is compared in real-time with the known pre-determined frequency for the metallic-tip; and u. if a detected (received) frequency by acoustic sensor/s correlates with a known frequency of the metallic tip of the wire, the targeted metallic tip of the wire on the B-mode image is color-coded using a predetermined color scheme and coordinates of a site within the body is determined based on a snap-shot or continuous readout from every sensor using certain triangulation techniques to provide a point-in-time or continuous detection of the metallic tip when the metallic tip is moved through the body.

2. The non-invasive bi-modal ultrasound-based methodology in accordance with claim 1, further comprising soft body tissues which are impacted by an acoustic force delivered by a carrier ultrasound frequency that emit a response frequency of 1-50 Hz whereas the metallic tip of the wire emits frequencies in a range of 500 Hz to 20 KHz.

3. A non-invasive bi-modal ultrasound-based methodology system of identifying and positioning targets in three-dimensional space comprising:

a. attaching a micron-size metallic tip which functions as a target or marker to a thin polymeric wire that is inserted through a guided catheter into a blood vessel within a body;

b. placing one or more disposable stickers on the body around the area of; area of interest;

c. positioning a receiving sensor within each disposable sticker which is placed on the skin around the area of interest on the body and removably adhered to the skin around the area of interest on the body, each sensor respectively is separated from skin by a thin and acoustically transparent film which is firmly coupled to skin on the body by a layer of biocompatible adhesive surrounding the thin film on the sticker;

d. utilizing an imaging scanner with B-mode capability to scan the area of interest in the body creating a gray-scale B-mode image of the area of interest in the body where the polymeric wire is located within the blood vessel within the body;

e. the transmitted ultrasound frequency being varied from 1 MHz to 14 MHz covering a range of depths;

f. once an image of the area of interest is obtained, the area of interest in the body is marked and the system is turned into a simultaneously B-mode imaging and stimulation mode;

g. the area of interest in the body is then stimulated by a swept band of ultrasound frequencies generated by specific sequences of acoustic energy schemes delivered by the same ultrasound imaging scanner as used in step "d";

h. the metallic tip of the wire traveling in the blood vessel within the body is stimulated by said acoustic energy resulting in emanating a band of characteristic response frequencies proportional to its material and size;

i. monitoring the response of the tip of the wire in real time so that a spectrum including a peak resonant frequency is recorded and spectrally analyzed;

j. having a detected peak resonant frequency correlated with a predetermined database of peak resonant frequencies to determine presence of the metallic tip of the wire, which may be invisible on the B-mode image;

k. if the detected response frequency or band of frequencies correlate with peak value or values in a predefined frequency signature map, then exact three-dimensional coordinates of the area from where the response frequency or band of frequencies have been detected is marked on the B-mode image and colored according to particular predetermined color-coded scheme; and l. utilizing a certain specialized triangulation technique, the exact three dimensional position of the metallic tip of the wire in the body is determined at every point of time based on the signals received by the receiving sensors and analyzed respectively, with the exact three dimensional position of the metallic tip of the wire in the area of interest in the body continuously displayed on a B-mode image and recorded for future reference.

4. The non-invasive bi-modal ultrasound-based methodology in accordance with claim 3, further comprising the response frequencies of soft tissue in the body to an acoustic stimulation are in the range of 1-50 Hz whereas the metallic tip of the wire emits frequencies in the range of 500 Hz to 20 KHz.

5. A non-invasive bi-modal ultrasound-based methodology of identifying and positioning targets in three-dimensional space comprising:
   a. attaching a micron-size metallic tip which functions as a known target to a thin polymeric wire that is inserted through a guided catheter into a blood vessel within a body;
   b. positioning a multiplicity of acoustic receiving sensors on a sensor retaining means so that the acoustic receiving sensors are spaced apart from each other;
   c. positioning the sensor retaining means on and around an area of interest on the body so that the multiplicity of acoustic receiving sensors are positioned on the body;
   d. utilizing a bi-modal image-based dynamic ultrasound spectrography functional imaging system which has an Imaging Mode and a Stimulation Mode;
   e. utilizing the Imaging Mode of the image-based dynamic ultrasound spectrography with a modified ultrasound imaging scanner to scan different segments of the area of the interest and impact the area of interest with ultrasound imaging frequencies in a range of 1 megahertz to 14 megahertz to image segments of the body at given times to thereby create an ultrasound B-mode gray scale image wherein ultrasound frequencies are transmitted toward specific segments of the body and subsequently reflected from each specific segment of the body toward the scanner;
   f. utilizing the Stimulation Mode of the image-based dynamic ultrasound spectrography with said modified ultrasound imaging scanner and stimulating selected segments of the body with a non-invasive chirp scheme delivered by the modified ultrasound imaging scanner utilizing two signal generators so that a first signal generator provides chirps of different frequency ranges while a second signal generator provides a fixed frequency so that due to any difference in any applied frequencies, certain acoustic radiation forces are generated proportional to a natural frequency of the targeted metallic tip of a polymeric wire that stimulates and vibrates the targeted metallic tip;
   g. a single chirp is broken down into different segments so that a frequency scan occurs in a particular and controlled sequence called "one presentation" so that the chirps can scan any desired frequency spans and search for any resonance of the targeted metallic tip in order to maximize the time for which each frequency span is introduced to thereby increase a signal-to-noise ratio;
   h. a stimulation signal is swept over a band of Hertz or kilohertz range frequencies and the frequencies are modulated on a megahertz ultrasound carrier frequency so that the metallic tip of a polymeric wire produces acoustic signals specific to their mass density and that are received by the acoustic receiving sensors and read out by an acoustic readout means to obtain response frequencies; and
   i. real-time comparing and correlating any obtained response frequencies with a predetermined map of peak frequencies corresponding to the same metallic tip of a polymeric wire so that when a detected frequency correlates with a predetermined frequency in a frequency signature map, the targeted site ef with the targeted metallic tip on the B-mode image is color-coded utilizing a predetermined color scheme and exact coordinates of a site within the body is determined.

6. The non-invasive bi-modal ultrasound-based methodology in accordance with claim 5, further comprising exact coordinates of a site within the body is determined based on a snap-shot or any continuous readouts from each of the acoustic receiving sensors and utilizing triangulation techniques.

7. The non-invasive bi-modal ultrasound-based methodology in accordance with claim 5, further comprising said sensor retaining means is a compliant sticker which houses each of the multiplicity of acoustic receiving sensors.

8. The non-invasive bi-modal ultrasound-based methodology in accordance with claim 7, further comprising at least three acoustic receiving sensors each respectively placed in and around the area of interest on in the body into which a micron-size metallic tip has been placed.

9. The non-invasive bi-modal ultrasound-based methodology in accordance with claim 5, further comprising each acoustic receiving sensor has a thin transparent biocompatible plastic film on a surface adjacent to the body to separate each respective acoustic receiving sensor from a location at which the acoustic receiving sensors were located on the body.

10. The non-invasive bi-modal ultrasound-based methodology in accordance with claim 9, further comprising biocompatible material on and around each biocompatible plastic film.

11. The non-invasive bi-modal ultrasound-based methodology in accordance with claim 10, further comprising each biocompatible adhesive material is covered by a removable protective material.

12. A non-invasive bi modal ultrasound-based methodology of identifying and positioning targets in three-dimensional space comprising:
   a. attaching a micron-size metallic tip which functions as a known target to a thin polymeric wire that is inserted through a guided catheter into a blood vessel within a body;
   b. positioning a multiplicity of acoustic receiving sensors, each firmly housed on a sensor retaining means so that the acoustic receiving sensors are spaced apart from each other;
   c. positioning the sensor retaining means on and around an area of interest on the body;
   d. utilizing a bi-modal image-based dynamic ultrasound spectrography functional imaging system which has an Imaging Mode and a Stimulation Mode;
   e. utilizing the Imaging Mode of the image-based dynamic ultrasound spectrography with a modified ultrasound imaging scanner to scan different segments of the area of interest on the human body and impact the body with ultrasound imaging frequencies in a range of 1 megahertz to 14 megahertz to image segments of the body at given times to thereby create an ultrasound B-mode gray scale image wherein ultrasound frequencies are transmitted toward specific segments of the body and subsequently reflected from each specific segment of body toward the scanner;
   f. utilizing the Stimulation Mode of the image-based dynamic ultrasound spectrography with said modified ultrasound imaging scanner and stimulating selected segments of the body with a non-invasive burst sweep form so that data is acquired over time wherein a fixed megahertz burst frequency is applied to the targeted polymeric wire with a micron-size metallic tip and another different megahertz frequency is incremented to obtain a first-hand estimate of the response frequency;
   g. a stimulation signal is swept over a band of Hertz or kilohertz range frequencies and the frequencies are modulated on a megahertz ultrasound carrier frequency so that targeted metallic tip produces and emits acoustic signal or signals specific to its material and size and that any acoustic signal or signals are received by the acoustic receiving sensors and read out by an acoustic readout means to obtain and display the received response frequencies; and h. real-time and continuous comparing and correlating any obtained response frequency or frequencies with a predetermined map of peak resonant frequencies corresponding to similar metallic tip so that when a detected frequency correlates with a predetermined frequency in a frequency signature map, a targeted site on the B-mode image is color-coded utilizing a predetermined color scheme and exact coordinates of the site containing the metallic tip of a thin polymeric wire within the body is determined.

13. The non-invasive bi-modal ultrasound-based methodology in accordance with claim 12, further comprising exact coordinates of a site within the body are determined based on snap-shot or continuous readouts from each of the acoustic receiving sensors and utilizing triangulation techniques.

14. The non-invasive bi-modal ultrasound-based methodology in accordance with claim 12, further comprising said sensor retaining means are multiple stickers which contain housings to respectively firmly retain each of the multiplicity of acoustic receiving sensors.

15. The non-invasive bi-modal ultrasound-based methodology in accordance with claim 14, further comprising at least three acoustic receiving sensors each respectively placed in a housing within the sticker wherein the housings are spaced apart.

16. The non-invasive bi-modal ultrasound-based methodology in accordance with claim 12, further comprising each acoustic receiving sensor has a thin transparent biocompatible plastic film on a body side surface to separate each respective acoustic receiving sensor from a location on the skin where an acoustic sensor has been placed.

17. The non-invasive bi-modal ultrasound-based methodology in accordance with claim 16 further comprising biocompatible adhesive material on and around each biocompatible plastic film.

18. The non-invasive bi-modal ultrasound-based methodology in accordance with claim 17, further comprising each biocompatible adhesive material is covered by a removable protective material.

19. A non-invasive bi-modal ultrasound-based methodology of identifying and positioning targets in three-dimensional space comprising:
   a. attaching a micron-size metallic tip which functions as a known target to a thin polymeric wire that is inserted through a guided catheter into a blood vessel within a body;
   b. positioning a multiplicity of acoustic receiving sensors each on a sensor retaining means so that the acoustic receiving sensors are spaced apart from each other;
   c. positioning the sensor retaining means on and around an area of interest on the body;
   d. utilizing an ultrasound imaging scanner with B-mode capability to scan the area of interest creating a gray-scale B-mode image of the area of interest with potential location of the thin polymeric wire;
   e. a transmitted ultrasound imaging frequency being varied from 1 MHz to 14 MHz covering a range of depths within the body;
   f. once an image of the area of interest is obtained, the scanner is maintained stationary relative to the body surface, the area of interest on the body is marked and interrogated;
   g. the area of interest in the body is then stimulated by a swept band of modulated frequencies generated by specific sequences of acoustic energy schemes delivered by the same ultrasound imaging scanner as in step "d";
   h. the metallic tip of the thin polymeric wire is then stimulated by sequential frequency schemes resulting in emanating a characteristic response frequency proportional to its material and size;
   i. real-time and continuous monitoring of any response so that a spectrum including a peak resonant frequency is recorded and spectrally analyzed; and
   j. having any detected peak response frequency correlated with a predetermined database of predefined peak resonant frequencies to determine presence of the metallic tip of the micron-size polymeric wire in the blood vessel within the body.

20. The non-invasive bi-modal ultrasound-based methodology in accordance with claim 19, further comprising said sensor retaining means are multiple stickers which contain housings to respectively and firmly retain each of the multiplicity of acoustic retaining reusable sensors.

21. The non-invasive bi-modal ultrasound-based methodology in accordance with claim 20 further comprising at least three reusable acoustic receiving sensors each respectively and firmly placed in a housing wherein the housings are spaced apart.

22. The non-invasive bi-modal ultrasound-based methodology in accordance with claim 19, further comprising each respective reusable acoustic receiving sensor is separated from the location on skin where each respective acoustic receiving sensor was placed by a thin transparent biocompatible plastic film.

23. The non-invasive bi-modal ultrasound-based methodology in accordance with claim 22, further comprising biocompatible adhesive material on and around each biocompatible plastic film.

24. The non-invasive bi-modal ultrasound-based methodology in accordance with claim 23, wherein further comprising each biocompatible self adhesive material is covered by a removable protective material.

25. The non-invasive modal ultrasound-based methodology in in accordance with claim 19, further comprising response frequencies of soft tissue within a body to a modulated acoustic stimulation signal is in a range of 1-50 Hz whereas the metallic tip of the wire emits response frequencies in a range of 500 Hz to 20 KHz.

26. The method non-invasive modal ultrasound-based methodology in in accordance with claim 19, further comprising:
   k. if the detected response frequency or band of frequencies correlate with the peak value or values in a predefined resonant frequency signature map, the exact three-dimensional location coordinates of the area from where the frequency or frequencies have been detected is marked on the B-mode image and colored according to a particular predetermined color-coded scheme; and
   l. utilizing a certain specialized triangulation technique, the exact three-dimensional position of the area of interest within the body is determined based on the signals received by the acoustic receiving sensors and analyzed respectively in real-time, with the exact three dimensional position of the metallic tip of the wire displayed on a B-mode image and recorded for future reference.

27. The non-invasive method in accordance with claim 19, further comprising each respective acoustic receiving sensor is reusable.

* * * * *